(12) United States Patent
Vargas-Voracek

(10) Patent No.: US 8,939,917 B2
(45) Date of Patent: Jan. 27, 2015

(54) METHODS AND DEVICES FOR QUANTITATIVE ANALYSIS OF BONE AND CARTILAGE

(75) Inventor: Rene Vargas-Voracek, Sunnyvale, CA (US)

(73) Assignee: ImaTx, Inc., Bedford, MA (US)

( * ) Notice: Subject to any disclaimer, the term of this patent is extended or adjusted under 35 U.S.C. 154(b) by 650 days.

(21) Appl. No.: 12/706,297

(22) Filed: Feb. 16, 2010

(65) Prior Publication Data

US 2010/0210972 A1   Aug. 19, 2010

Related U.S. Application Data

(60) Provisional application No. 61/152,440, filed on Feb. 13, 2009.

(51) Int. Cl.
| | |
|---|---|
| A61B 5/103 | (2006.01) |
| A61B 5/117 | (2006.01) |
| G01B 1/00 | (2006.01) |
| A61B 1/00 | (2006.01) |
| G09B 23/28 | (2006.01) |
| A61B 5/00 | (2006.01) |

(52) U.S. Cl.
CPC .............. *A61B 5/4528* (2013.01); *A61B 5/4514* (2013.01)
USPC ............... 600/587; 33/511; 33/512; 434/262; 434/267; 434/274

(58) Field of Classification Search
USPC ............ 600/587; 434/86, 262, 267, 274, 275; 33/511, 512; 606/102; 700/110, 118
See application file for complete search history.

(56) References Cited

U.S. PATENT DOCUMENTS

| | | | |
|---|---|---|---|
| 2,274,808 A | 3/1942 | Rinn | 250/69 |
| 3,924,133 A | 12/1975 | Reiss | 250/408 |
| 4,012,638 A | 3/1977 | Altschuler et al. | 250/491 |
| 4,126,789 A | 11/1978 | Vogl et al. | 250/505 |
| 4,233,507 A | 11/1980 | Volz | 250/252 |
| 4,251,732 A | 2/1981 | Fried | 250/479 |
| 4,298,800 A | 11/1981 | Goldman | 250/445 T |
| 4,356,400 A | 10/1982 | Polizzi et al. | 378/138 |
| 4,400,827 A | 8/1983 | Spears | 378/207 |
| 4,593,400 A | 6/1986 | Mouyen | 378/99 |
| 4,649,561 A | 3/1987 | Arnold | 378/207 |

(Continued)

FOREIGN PATENT DOCUMENTS

| | | | |
|---|---|---|---|
| CA | 2342344 | 3/2000 | G06K 9/00 |
| DE | 19853965 | 5/2000 | A61F 2/28 |

(Continued)

OTHER PUBLICATIONS

Burgkart et al., "Magnetic Resonance Imaging-Based Assessment of Cartilage Loss in Severe Osteoarthritis". Arthritis and Rheumatism, vol. 44, No. 9, Sep. 2001, pp. 2072-2077.*

(Continued)

*Primary Examiner* — Devin Henson
(74) *Attorney, Agent, or Firm* — Sunstein Kann Murphy & Timbers LLP

(57) ABSTRACT

A method for measuring cartilage defects within a subject includes surgically exposing a joint or cartilage surface. The exposed joint or cartilage surface having at least one defect, and the method may generating a cast of the at least one defect. The method may also include measuring a parameter of the cast, thereby estimating a characteristic of the defect.

19 Claims, 10 Drawing Sheets

(56) References Cited

U.S. PATENT DOCUMENTS

| | | | |
|---|---|---|---|
| 4,686,695 A | 8/1987 | Macovski | 378/146 |
| 4,721,112 A | 1/1988 | Hirano et al. | 128/659 |
| 4,782,502 A | 11/1988 | Schulz | 378/18 |
| 4,922,915 A | 5/1990 | Arnold et al. | 128/653 R |
| 4,956,859 A | 9/1990 | Lanza et al. | 378/157 |
| 4,985,906 A | 1/1991 | Arnold | 378/18 |
| 5,001,738 A | 3/1991 | Brooks | 378/170 |
| 5,090,040 A | 2/1992 | Lanza et al. | 378/62 |
| 5,122,664 A | 6/1992 | Ito et al. | 250/327.2 |
| 5,127,032 A | 6/1992 | Lam et al. | 378/189 |
| 5,150,394 A | 9/1992 | Karellas | 378/62 |
| 5,172,695 A | 12/1992 | Cann et al. | 128/653.1 |
| 5,187,731 A | 2/1993 | Shimura | 378/207 |
| 5,200,993 A | 4/1993 | Wheeler et al. | 379/96 |
| 5,222,021 A | 6/1993 | Feldman et al. | 364/413.14 |
| 5,228,445 A | 7/1993 | Pak et al. | 128/660.01 |
| 5,235,628 A | 8/1993 | Kalender | 378/207 |
| 5,247,934 A | 9/1993 | Wehrli et al. | 128/653.2 |
| 5,270,651 A | 12/1993 | Wehrli | 324/308 |
| 5,271,401 A | 12/1993 | Fishman | 128/654 |
| 5,281,232 A | 1/1994 | Hamilton et al. | 606/130 |
| 5,320,102 A | 6/1994 | Paul et al. | 128/653.2 |
| 5,335,260 A | 8/1994 | Arnold | 378/207 |
| 5,384,643 A | 1/1995 | Inga et al. | 358/403 |
| 5,476,865 A | 12/1995 | Panetta et al. | 514/369 |
| 5,493,593 A | 2/1996 | Müller et al. | 378/19 |
| 5,493,601 A | 2/1996 | Fivez et al. | 378/207 |
| 5,513,240 A | 4/1996 | Hausmann et al. | 378/170 |
| 5,521,955 A | 5/1996 | Gohno et al. | 378/18 |
| 5,533,084 A | 7/1996 | Mazess | 378/54 |
| 5,537,483 A | 7/1996 | Stapleton et al. | 382/309 |
| 5,562,448 A | 10/1996 | Mushabac | 433/215 |
| 5,565,678 A | 10/1996 | Manian | 250/252.1 |
| 5,592,943 A | 1/1997 | Buhler et al. | 128/661.03 |
| 5,594,775 A | 1/1997 | Hangartner | 378/207 |
| 5,600,574 A | 2/1997 | Reitan | 364/552 |
| 5,657,369 A | 8/1997 | Stein et al. | 378/208 |
| 5,673,298 A | 9/1997 | Mazess | 378/54 |
| 5,687,210 A | 11/1997 | Maitrejean et al. | 378/57 |
| 5,769,072 A | 6/1998 | Olsson et al. | 128/205.13 |
| 5,769,074 A | 6/1998 | Barnhill et al. | 128/630 |
| 5,772,592 A | 6/1998 | Cheng et al. | 600/407 |
| 5,852,647 A | 12/1998 | Schick et al. | 378/53 |
| 5,864,146 A | 1/1999 | Karellas | 250/581 |
| 5,886,353 A | 3/1999 | Spivey et al. | 250/370.09 |
| 5,915,036 A | 6/1999 | Grunkin et al. | 382/132 |
| 5,917,877 A | 6/1999 | Chiabrera et al. | 378/5.3 |
| 5,919,808 A | 7/1999 | Petrie et al. | 514/372 |
| 5,931,780 A | 8/1999 | Giger et al. | 600/407 |
| 5,945,412 A | 8/1999 | Fuh et al. | 514/176 |
| 5,948,692 A | 9/1999 | Miyauti et al. | 436/501 |
| 6,013,031 A | 1/2000 | Mendlein et al. | 600/442 |
| 6,029,078 A | 2/2000 | Weinstein et al. | 600/407 |
| 6,064,716 A | 5/2000 | Siffert et al. | 378/53 |
| 6,077,224 A | 6/2000 | Lang et al. | 600/437 |
| 6,108,635 A | 8/2000 | Herren et al. | 705/2 |
| 6,156,799 A | 12/2000 | Hartke et al. | 514/573 |
| 6,178,225 B1 | 1/2001 | Zur et al. | 378/98.2 |
| 6,205,348 B1 | 3/2001 | Giger et al. | 600/407 |
| 6,215,846 B1 | 4/2001 | Mazess et al. | 378/62 |
| 6,226,393 B1 | 5/2001 | Grunkin et al. | 382/128 |
| 6,246,745 B1 | 6/2001 | Bi et al. | 378/54 |
| 6,248,063 B1 | 6/2001 | Barnhill et al. | 600/300 |
| 6,249,692 B1 | 6/2001 | Cowin | 600/407 |
| 6,252,928 B1 | 6/2001 | MacKenzie | 378/54 |
| 6,285,901 B1 | 9/2001 | Taicher et al. | 600/410 |
| 6,289,115 B1 | 9/2001 | Takeo | 382/130 |
| 6,302,582 B1 | 10/2001 | Nord et al. | 378/207 |
| 6,306,087 B1 | 10/2001 | Barnhill et al. | 600/300 |
| 6,306,822 B1 | 10/2001 | Kumagai et al. | 514/7 |
| 6,315,553 B1 | 11/2001 | Sachdeva et al. | 433/24 |
| 6,320,931 B1 | 11/2001 | Arnold | 378/56 |
| 6,377,653 B1 | 4/2002 | Lee et al. | 378/54 |
| 6,405,068 B1 | 6/2002 | Pfander et al. | 600/407 |
| 6,411,729 B1 | 6/2002 | Grunkin | 382/128 |
| 6,430,427 B1 | 8/2002 | Lee et al. | 600/407 |
| 6,442,287 B1 | 8/2002 | Jiang et al. | 382/128 |
| 6,449,502 B1 | 9/2002 | Ohkubo | 600/407 |
| 6,463,344 B1 | 10/2002 | Pavloskaia et al. | 700/98 |
| 6,490,476 B1 | 12/2002 | Townsend et al. | 600/427 |
| 6,501,827 B1 | 12/2002 | Takasawa | 378/116 |
| 6,556,698 B1 | 4/2003 | Diano et al. | 382/132 |
| 6,633,772 B2 | 10/2003 | Ford et al. | 600/345 |
| 6,690,761 B2 | 2/2004 | Lang et al. | 378/56 |
| 6,694,047 B1 | 2/2004 | Farrokhnia et al. | 382/132 |
| 6,717,174 B2 | 4/2004 | Karellas | 250/582 |
| 6,775,401 B2 | 8/2004 | Hwang et al. | 382/131 |
| 6,799,066 B2 | 9/2004 | Steines et al. | 600/407 |
| 6,807,249 B2 | 10/2004 | Dinten et al. | 378/54 |
| 6,811,310 B2 | 11/2004 | Lang et al. | 378/169 |
| 6,824,309 B2 | 11/2004 | Robert-Coutant et al. | 378/207 |
| 6,829,378 B2 | 12/2004 | DiFilippo et al. | 382/128 |
| 6,835,377 B2 | 12/2004 | Goldberg et al. | 424/93.7 |
| 6,836,557 B2 | 12/2004 | Tamez-Pena et al. | 382/128 |
| 6,895,077 B2 | 5/2005 | Karellas et al. | 378/98.3 |
| 6,904,123 B2 | 6/2005 | Lang | 378/54 |
| 6,934,590 B2 | 8/2005 | Ogawa | 700/19 |
| 6,975,894 B2 | 12/2005 | Wehrli et al. | 600/407 |
| 7,050,534 B2 | 5/2006 | Lang | 378/54 |
| 7,058,159 B2 | 6/2006 | Lang et al. | 378/54 |
| 7,079,681 B2 | 7/2006 | Lee et al. | 382/162 |
| 7,088,847 B2 | 8/2006 | Craig et al. | 382/110 |
| 7,120,225 B2 | 10/2006 | Lang et al. | 378/54 |
| 7,184,814 B2 | 2/2007 | Lang et al. | 600/416 |
| 7,239,908 B1 | 7/2007 | Alexander et al. | 600/427 |
| 7,245,697 B2 | 7/2007 | Lang | 378/54 |
| 7,283,857 B1 | 10/2007 | Fallon et al. | 600/407 |
| 7,292,674 B2 | 11/2007 | Lang | 378/54 |
| 7,379,529 B2 | 5/2008 | Lang | 378/54 |
| 7,467,892 B2 | 12/2008 | Lang et al. | 378/207 |
| 7,486,919 B2 | 2/2009 | Furuya | 399/313 |
| 7,545,964 B2 | 6/2009 | Lang et al. | 382/128 |
| 7,580,504 B2 | 8/2009 | Lang et al. | 378/56 |
| 7,636,459 B2 * | 12/2009 | Dore et al. | 382/128 |
| 7,660,453 B2 | 2/2010 | Lang | 382/132 |
| 7,664,298 B2 | 2/2010 | Lang et al. | 382/128 |
| 7,676,023 B2 | 3/2010 | Lang | 378/54 |
| 7,840,247 B2 | 11/2010 | Liew et al. | 600/407 |
| 7,848,558 B2 | 12/2010 | Giger et al. | 382/128 |
| 7,995,822 B2 | 8/2011 | Lang et al. | 382/128 |
| 8,000,441 B2 | 8/2011 | Lang et al. | 378/56 |
| 8,000,766 B2 | 8/2011 | Lang et al. | 600/407 |
| 8,031,836 B2 | 10/2011 | Lang et al. | 378/54 |
| 8,068,580 B2 | 11/2011 | Lang et al. | 378/54 |
| 8,073,521 B2 | 12/2011 | Liew et al. | 600/407 |
| 8,260,018 B2 | 9/2012 | Lang et al. | 382/128 |
| 8,290,564 B2 | 10/2012 | Lang et al. | 600/407 |
| 8,377,016 B2 * | 2/2013 | Argenta et al. | 604/305 |
| 8,588,365 B2 | 11/2013 | Lang et al. | 378/56 |
| 8,600,124 B2 | 12/2013 | Arnaud et al. | 382/128 |
| 8,617,175 B2 | 12/2013 | Park et al. | 606/89 |
| 8,625,874 B2 | 1/2014 | Lang et al. | 382/132 |
| 8,639,009 B2 | 1/2014 | Lang et al. | 382/132 |
| 8,649,481 B2 | 2/2014 | Lang et al. | 378/54 |
| 2001/0020240 A1 | 9/2001 | Classen | 707/104.1 |
| 2002/0082779 A1 | 6/2002 | Ascenzi | 702/19 |
| 2002/0087274 A1 | 7/2002 | Alexander et al. | 702/19 |
| 2002/0114425 A1 | 8/2002 | Lang et al. | 378/56 |
| 2002/0159567 A1 | 10/2002 | Sako et al. | 378/117 |
| 2002/0186818 A1 | 12/2002 | Arnaud et al. | 378/165 |
| 2002/0188297 A1 | 12/2002 | Dakin et al. | 606/72 |
| 2002/0194019 A1 | 12/2002 | Evertsz | 705/2 |
| 2002/0196966 A1 | 12/2002 | Jiang et al. | 382/132 |
| 2003/0015208 A1 | 1/2003 | Lang et al. | 128/922 |
| 2003/0133601 A1 | 7/2003 | Giger et al. | 382/128 |
| 2003/0158159 A1 | 8/2003 | Schwartz | 514/170 |
| 2003/0175680 A1 | 9/2003 | Allard et al. | 435/4 |
| 2003/0198316 A1 | 10/2003 | Dewaele et al. | 378/54 |
| 2004/0009459 A1 | 1/2004 | Anderson et al. | 434/262 |
| 2004/0106868 A1 | 6/2004 | Liew et al. | 600/442 |
| 2004/0114789 A1 | 6/2004 | Saha et al. | 382/128 |
| 2004/0204760 A1 * | 10/2004 | Fitz et al. | 623/14.12 |
| 2004/0247074 A1 | 12/2004 | Langton | 378/54 |
| 2004/0254439 A1 | 12/2004 | Fowkes et al. | 600/407 |

(56) References Cited

U.S. PATENT DOCUMENTS

| | | | |
|---|---|---|---|
| 2005/0015002 A1 | 1/2005 | Dixon et al. | 600/407 |
| 2005/0037515 A1 | 2/2005 | Nicholson et al. | 436/173 |
| 2005/0059887 A1 | 3/2005 | Mostafavi et al. | 600/427 |
| 2005/0148860 A1 | 7/2005 | Liew et al. | 600/410 |
| 2005/0203384 A1 | 9/2005 | Sati et al. | 600/426 |
| 2005/0240096 A1 | 10/2005 | Ackerman et al. | 600/410 |
| 2006/0062442 A1 | 3/2006 | Arnaud et al. | 382/128 |
| 2007/0047794 A1 | 3/2007 | Lang et al. | 382/132 |
| 2007/0156066 A1* | 7/2007 | McGinley et al. | 600/587 |
| 2007/0274442 A1 | 11/2007 | Gregory et al. | 378/54 |
| 2008/0031412 A1 | 2/2008 | Lang et al. | 378/54 |
| 2008/0058613 A1 | 3/2008 | Lang et al. | 600/300 |
| 2008/0097794 A1 | 4/2008 | Arnaud et al. | 705/3 |
| 2008/0219412 A1 | 9/2008 | Lang | 378/54 |
| 2009/0207970 A1 | 8/2009 | Lang | 378/207 |
| 2009/0225958 A1 | 9/2009 | Lang | 378/207 |
| 2010/0014636 A1 | 1/2010 | Lang et al. | 378/56 |
| 2010/0098212 A1 | 4/2010 | Lang | 378/54 |
| 2010/0130832 A1 | 5/2010 | Lang et al. | 600/300 |
| 2010/0197639 A1 | 8/2010 | Lang et al. | 514/143 |
| 2010/0210972 A1 | 8/2010 | Vargas-Voracek | 600/587 |
| 2011/0036360 A1 | 2/2011 | Lang et al. | 128/898 |
| 2011/0040168 A1 | 2/2011 | Arnaud et al. | 600/407 |
| 2011/0105885 A1 | 5/2011 | Liew et al. | 600/410 |
| 2012/0027283 A1 | 2/2012 | Lang et al. | 382/132 |
| 2012/0063568 A1 | 3/2012 | Lang et al. | 378/56 |
| 2012/0072119 A1 | 3/2012 | Lang et al. | 702/19 |
| 2012/0087468 A1 | 4/2012 | Lang et al. | 378/56 |
| 2013/0039592 A1 | 2/2013 | Lang et al. | 382/232 |
| 2013/0113802 A1 | 5/2013 | Weersink et al. | 345/427 |
| 2013/0195325 A1 | 8/2013 | Lang et al. | 382/128 |

FOREIGN PATENT DOCUMENTS

| | | | |
|---|---|---|---|
| EP | 0314506 | 5/1989 | A61B 6/14 |
| EP | 0797952 | 10/1997 | A61B 8/08 |
| EP | 0570936 | 8/2000 | A61B 8/08 |
| EP | 0678191 | 2/2001 | G01D 18/00 |
| EP | 1230896 | 8/2002 | A61B 6/14 |
| EP | 1283492 | 2/2003 | G06F 19/00 |
| EP | 1349098 | 10/2003 | G06F 19/00 |
| EP | 1357480 | 10/2003 | G06F 17/00 |
| EP | 1424650 | 6/2004 | G06F 19/00 |
| EP | 1598778 | 11/2005 | G06T 3/40 |
| EP | 1069395 | 7/2006 | G01B 3/10 |
| GB | 2023920 | 1/1980 | H01J 35/14 |
| JP | 62 266053 | 11/1987 | A61C 19/04 |
| JP | 05 099829 | 4/1993 | G01N 9/24 |
| JP | 08 186762 | 7/1996 | H04N 5/325 |
| JP | 10 145396 | 5/1998 | H04L 12/28 |
| JP | 10 262959 | 10/1998 | A61B 6/00 |
| JP | 11 069136 | 3/1999 | H04N 1/387 |
| JP | 11 112877 | 4/1999 | H04N 5/325 |
| JP | 2002 045722 | 2/2000 | B02C 18/42 |
| JP | 2000 126168 | 5/2000 | A61B 6/00 |
| JP | 2000 139889 | 5/2000 | A61B 6/00 |
| JP | 2003 230557 | 8/2003 | A61B 6/00 |
| WO | WO 94/012855 | 6/1994 | G01D 18/00 |
| WO | WO 95/014431 | 6/1995 | A61B 5/103 |
| WO | WO 99/008597 | 2/1999 | A61B 8/00 |
| WO | WO 99/045371 | 9/1999 | G01N 23/06 |
| WO | WO 99/052331 | 10/1999 | H05G 1/10 |
| WO | WO 00/033157 | 6/2000 | |
| WO | WO 00/072216 | 11/2000 | G06F 19/00 |
| WO | WO 01/038824 | 5/2001 | G01B 15/02 |
| WO | WO 01/063488 | 8/2001 | G06F 17/30 |
| WO | WO 01/065449 | 9/2001 | G06F 17/60 |
| WO | WO 02/017789 | 3/2002 | A61B 6/00 |
| WO | WO 02/022014 | 3/2002 | A61B 5/055 |
| WO | WO 02/030283 | 4/2002 | A61B 6/00 |
| WO | WO 02/096284 | 12/2002 | A61B 5/00 |
| WO | WO 03/071934 | 9/2003 | |
| WO | WO 03/073232 | 9/2003 | |
| WO | WO 03/088085 | 10/2003 | G06F 17/30 |
| WO | WO 2004/019256 | 3/2004 | G06F 19/00 |
| WO | WO 2004/025541 | 3/2004 | G06F 19/00 |
| WO | WO 2004/062495 | 7/2004 | A61B 5/00 |
| WO | WO 2004/086972 | 10/2004 | A61B 6/00 |
| WO | WO 2004/096048 | 11/2004 | A61B 6/00 |
| WO | WO 2005/027732 | 3/2005 | |
| WO | WO 2006/033712 | 3/2006 | A61B 6/00 |
| WO | WO 2006/034018 | 3/2006 | G06T 7/00 |
| WO | WO 2008/034101 | 3/2008 | |
| WO | WO 99/045845 | 9/2009 | A61B 8/00 |

OTHER PUBLICATIONS

Burgkart et al., "Magnetic Resonance Imaging-Based Assessment of Cartilage Loss in Severe Osteoarthritis", Arthritis & Rheumatism, vol. 44, No. 9, Sep. 2001, pp. 2072-2077.*

Barker, "Case Method: Entity Relationship Modeling" (Computer Aided Systems Engineering), $1^{st}$ Ed., Addison-Wesley Longman Pub. Co., Inc., publisher, 2 pages (Abstract Pages Only) (1990).

Bauer et al., "Biochemical Markers of Bone Turnover and Prediction of Hip Bone Loss in Older Women: The Study of Osteoporotic Fractures," *Journal of Bone and Mineral Research*, vol. 14, pp. 1404-1410 (1999).

Beck et al., "Experimental Testing of a DEXA-Derived Curved Beam Model of the Proximal Femur," Journal of Orthopaedic Research, vol. 16, No. 3, pp. 394-398 (1998).

Black et al., "An Assessment Tool for Predicting Fracture Risk in Postmenopausal Women" *Osteoporosis International*, vol. 12, pp. 519-528 (2001).

Blake et al., "Active Contours; The Application of Techniques from Graphics, Vision, Control Theory and Statistics to Visual Tracking of Shapes in Motion," Title page and Table of Contents pages only, 6 pages (1999).

Bushberg et al., "The Essential Physics of Medical Imaging," Lipincott, Williams & Wilkins, Title page and Table of Contents pages only, 3 pages (1994).

Cann, "Quantitative CT for Determination of Bone Mineral Density: A Review," Radiology, vol. 166, No. 2, pp. 509-522 (1988).

Castleman, "Digital Image Processing," Prentice Hall, Title page and Table of Contents pages only, 9 pages (1996).

Cheal et al., "Role of Loads & Prosthesis Material Properties on the Mechanics of the Proximal Femur After Total Hip Arthroplasty," *J. Orthop. Res.*, vol. 10, No. 3, pp. 405-422 (1992).

Cootes et al., "Anatomical statistical models and their role in feature extraction," *The British Journal of Radiology*, Special Issue, 7 pages [S133-S139] (2004).

Cootes et al., "Statistical models of appearance for medical image analysis and computer vision," *Proc. SPIE Medical Imaging*, 14 pages, (2001).

Cootes, "An Introduction to Active Shape Models," *Image Processing and Analysis*, Ch. 7, pp. 1-26 (2000).

Cortet et al., "Bone Microarchitecture and Mechanical Resistance," *Joint Bone Spine*, vol. 68, pp. 297-305 (2001).

Crabtree et al., "Improving Risk Assessment: Hip Geometry, Bone Mineral Distribution and Bone Strength in Hip Fracture Cases and Controls. The EPOS Study," *Osteoporos Int*, vol. 13, pp. 48-54 (2002).

Crawley, "In Vivo Tissue Characterization Using Quantitative Computed Tomography: A Review," *Journal of Medical Engineering & Technology*, vol. 14, No. 6, pp. 233-242 (1990).

Cummings et al., "Bone Density at Various Sites for Prediction of Hip Fractures," *The Lancet*, vol. 341, pp. 72-75 (1993).

Davies et al., "A Minimum Description Length Approach to Statistical Shape Modeling," IEEE Transaction on Medical Imaging, vol. 21, No. 5, pp. 525-537 (2002).

Duryea et al., "New radiographic-based surrogate outcome measures for osteoarthritis of the knee," *Osteoarthritis and Cartilage*, vol. 11, pp. 102-110 (2003).

Duryea et al., "Trainable rule-based algorithm for the measurement of joint space width in digital radiographic images of the knee," *Medical Physics*, vol. 27, No. 3, pp. 580-591 (2000).

Eastell, "Treatment of Postmenopausal Osteoporosis," *New Engl. J. of Med.*, vol. 338, No. 11, pp. 736-746 (1988).

(56) References Cited

OTHER PUBLICATIONS

Engelman et al., "Impact of Geographic Barriers on the Utilization of Mammograms by Older Rural Women, " *Journal of the American Geriatrics Society*, vol. 50, No. 1, pp. 62-68 (2002).
Faulkner, "Bone Densitometry: Choosing the Proper Skeletal Site to Measure," *J. Clin. Densitometry*, vol. 1, No. 3, pp. 279-285 (1998).
Fleute et al., "Incorporating a statistically based shape model into a system for computer-assisted anterior cruciate ligament surgery," *Medical Image Analysis*, vol. 3, No. 3, pp. 209-222 (1999).
Fleute et al., "Statistical model registration for a C-arm CT system," Computer Science Department, The Johns Hopkins University, pp. 1667-1670 (2002).
Fleute et al. "Nonrigid 3-D/2-D Registration of Images Using Statistical Models," pp. 138-147 (1999).
Geraets et al. "A New Method for Automatic Recognition of the Radiographic Trabecular Pattern," *J. Bone and Min. Res.*, Department of Oral Radiology, Academic Center for Dentistry Amsterdam (ACTA), vol. 3, No. 3, pp. 227-233 (1990).
Gilliland et al., "Patterns of Mammography Use Among Hispanic, American Indian, and Non-Hispanic White Women in New Mexico, 1994-1997," *American Journal of Epidemiology*, vol. 152, No. 5, pp. 432-437 (2000).
Gluer et al., Peripheral Measurement Techniques for the Assessment of Osteoporosis, *Semin. Nucl. Med.*, vol. 27, No. 3, pp. 229-247 (1997).
Gluer, "Quantitative Ultrasound Techniques for the Assessment of Osteoporosis: Expert Agreement on Current Status," *J. Bone Miner. Res.*, vol. 12, No. 8, pp. 1280-1288 (1997).
Grisso et al., "Risk Factors for Falls as a Cause of Hip Fracture in Women. The Northeast Hip Fracture Study Group," *N. Engl. J. Med.*, (Abstract Page Only), 1 page, vol. 324, No. 19 (1991).
Gudmundsdottir et al., "Vertebral Bone Density in Icelandic Women Using Quantitative Computed Tomography Without an External Reference Phantom," *Osteoporosis Int.*, vol. 3, pp. 84-89 (1993).
Hayes et al., "Biomechanics of Cortical and Trabecular Bone: Implications for Assessment of Fracture Risk," *Basic Orthopaedic Biomechanics*, 2nd Ed., Ch. 3, pp. 69-111, Lippincott-Raven, publishers (1997).
Hayes et al., "Biomechanics of Fracture Risk Prediction of the Hip and Spine by Quantitative Computed Tomography," *Radiologic Clinics of North America*, vol. 29, No. 1, pp. 1-18 (1991).
Hayes et al., "Impact Near the Hip Dominates Fracture Risk in Elderly Nursing Home Residents Who Fall," *Calcif. Tissue Int.* (Abstract Page Only), 1 page, vol. 52, No. 3 (1993).
Hedström et al., "Biochemical Bone Markers and Bone Density in Hip Fracture Patients," *Acta Orthop. Scand.*, vol. 71, No. 4, pp. 409-413 (2000).
Horn, "Closed-form solution of absolute orientation using unit quaernions," *J. Opt. Soc. of Am. A*, vol. 4, No. 4, pp. 629-642 (1987).
Hosking et al., "Prevention of Bone Loss with Alendronate in Postmenopausal Women Under 60 Years of Age," *N. Engl. J. Med.*, vol. 338, No. 8, pp. 485-492 (1998).
Ikuta et al., "Quantitative Analysis Using the Star Volume Method Applied to Skeleton Patterns Extracted with a Morphological Filter," *Journal of Bone and Mineral Metabolism*, vol. 18, pp. 271-277 (2000).
Jacobs et al., "Long-term Bone Mass Evaluation of Mandible and Lumbar Spine in a Group of Women Receiving Hormone Replacement Therapy," *European Journal Oral Sciences*, vol. 104, pp. 10-16 (1996).
Jazieh et al., "Mammography Utilization Pattern Throughout the State of Arkansas: A Challenge for the Future," *Journal of Community Health*, vol. 26, No. 4, pp. 249-255 (2001).
Jeffcoat et al., "Post-menopausal bone loss and its relationship to oral bone loss", *Periodontology*, vol. 23, pp. 94-102 (2000).
Klose, "Teleradiology—A Model for Remote Consultation," *Electromedica*, vol. 66, No. 1, pp. 37-41 (1998)
Kumasaka et al., "Initial Investigation of Mathematical Morphology for the Digital Extraction of the Skeletal Characteristics of Trabecular Bone," *Dept. of Oral Surgery and Oral and Maxillofacial Radiology*, Kanagawa Dental College, Japan, pp. 161-168 (1996).
Lam et al., "X-Ray Diagnosis: A Physician's Approach," Title/Copyright pages and Index pages only, 4 pages, Springer-Verlag, publisher (ISBN 9813083247) (1998).
Lang et al., "Osteoporosis—Current Techniques and Recent Developments in Quantitative Bone Densitometry" *Radiologic Clinics of North America*, vol. 29, No. 1, pp. 49-76 (1991).
Marshall et al., "Meta-Analysis of How Well Measures of Bone Mineral Density Predict Occurrence of Osteoporotic Fractures," *Br. Med. J.*, vol. 312, pp. 1254-1259 (1996).
Metrabio Website, "QUS-2 Calcaneal Ultrasonometer," What's New: Ultrasound, Retrieved from the Internet—http://www.metrabio.com/html/_prods/L3-ultrasound-r.ht, 2 pages (2001).
Mourtada et al., "Curved Beam Model of the Proximal Femur for Estimating Stress Using Dual-Energy X-Ray Absorptiometry Derived Structural Geometry," *J. Ortho. Res.*, vol. 14, No. 3, pp. 483-492 (1996).
Njeh et al., "The Role of Ultrasound in the Assessment of Osteoporosis: A Review," *Osteoporosis Int.*, vol. 7, pp. 7-22 (1997).
Njeh et al., "Quantitative Ultrasound: Assessment of Osteoporosis and Bone Status," Title page and Table of Contents pages only, 4 pages (1999).
Ouyang et al., "Morphometric Texture Analysis of Spinal Trabecular Bone Structure Assessed Using Orthogonal Radiographic Projections," *Med. Phys.*, vol. 25, No. 10, pp. 2037-2045 (1998).
Patel et al., "Radiation Dose to the Patient and Operator from a Peripheral Dual X-Ray Absorptiometry System," *Journal of Clinical Densitometry*, vol. 2, No. 4, pp. 397-401 (1999).
Pharoah, "X-Ray Film, Intensifying Screens, and Grids," Ch. 4, Section 4: Imaging Principles and Techniques, Oral Radiology, 4th ed., pp. 68-76 (2000).
Pinilla et al., "Impact Direction from a Fall Influences the Failure Load of the Proximal Femur as Much as Age-Related Bone Loss," *Calcified Tissue International*, vol. 58, pp. 231-235 (1996).
Riggs et al., "Changes in Bone Mineral Density of the Proximal Femur and Spine with Aging: Differences Between the Postmenopausal and Senile Osteoporosis Syndromes," *J. Clin. Invest.*, vol. 70, pp. 716-723 (1982).
Russ, "The Image Processing Handbook," $3^{rd}$ Edition, North Carolina State Univ., Chapter 7: Processing Binary Images, pp. 494-501 (1998).
Ruttiman et al., "Fractal Dimension from Radiographs of Peridontal Alveolar Bone: A Possible Diagnostic Indicator of Osteoporosis," *Oral Surg, Oral Med, Oral Pathol.*, vol. 74, No. 1, pp. 98-110 (1992).
Sandler et al., "An Analysis of the Effect of Lower Extremity Strength on Impact Severity During a Backward Fall," *Journal of Biomechanical Engineering*, vol. 123, pp. 590-598 (2001).
Shrout et al., "Comparison of Morphological Measurements Extracted from Digitized Dental Radiographs with Lumbar and Femoral Bone Mineral Density Measurements in Postmenopausal Women," *J. Periondontal*, vol. 71, No. 3, pp. 335-340 (2000).
Slone et al., "Body CT: A Practical Approach," Title page and Table of Contents pages only, 4 pages, McGraw-Hill, publisher (ISBN 007058219) (1999).
Southard et al., "Quantitative Features of Digitized Radiographic Bone Profiles," *Oral Surgery, Oral Medicine, and Oral Pathology*, vol. 73, No. 6, pp. 751-759 (1992).
Southard et al., "The Relationship Between the Density of the Alveolar Processes and that of Post-Cranial Bone," *J. Dent. Res.*, vol. 79, No. 4, pp. 964-969 (2000).
Stout et al., "X-Ray Structure Determination: A Practical Guide," 2nd Ed., Title page and Table of Contents pages only, 4 pages, John Wiley & Sons, publisher (ISBN 0471607118) (1989).
Svendsen et al., "Impact of Soft Tissue on In-Vivo Accuracy of Bone Mineral Measurements in the Spine, Hip, and Forearm: A Human Cadaver Study," *J. Bone Miner. Res.*, vol. 10, No. 6, pp. 868-873 (1995).
Tothill et al., "Errors due to Non-Uniform Distribution of Fat in Dual X-Ray Absorptiometry of the Lumbar Spine," *Br. J. Radiol.*, vol. 65, pp. 807-813 (1992).

(56) References Cited

OTHER PUBLICATIONS

Van den Kroonenberg et al., "Dynamic Models for Sideways Falls from Standing Height," *Journal of Biomechanical Engineering*, vol. 117, pp. 309-318 (1995).

Verhoeven et al., "Densitometric Measurement of the Mandible: Accuracy and Validity of Intraoral Versus Extraoral Radiographic Techniques in an In Vitro Study," *Clin. Oral Impl. Res.*, vol. 9, pp. 333-342 (1998).

White et al., "Alterations of the Trabecular Pattern in the Jaws of Patients with Osteoporosis," *Oral Surg., Oral Med., Oral Pathol., Oral Radiol., and Endod.*, vol. 88, pp. 628-635 (1999).

Yoshikawa et al., "Geometric Structure of the Femoral Neck Measured Using Dual-Energy X-Ray Absorptiometry," *J. Bone Miner. Res.*, vol. 10, No. 3, p. 510 (Abstract Only) (1995).

Hologic, Classic DXA Technology for the Office-based Practice, QDR-4000 Clinical Bone Densitometer, 8 pages, date unknown.

Majumdar et al., "Correlation of Trabecular Bone Structure with Age, Bone Mineral Density, and Osteoporotic Status: In Vivo Studies in the Distal Radius Using High Resolution Magnetic Resonance Imaging," Journal of Bone and Mineral Research, vol. 12, No. 1, pp. 111-118, 1997.

\* cited by examiner

| Tool Diameter (mm) | # defects | Average % Absolute error[1] | | Average %Error[2] | |
|---|---|---|---|---|---|
| | | Depth | Wax | Depth | Wax |
| 6.35 | 65.00 | 10.50 | 6.46 | 2.45 | 0.64 |
| 9.53 | 35.00 | 7.26 | 5.33 | 1.17 | 1.98 |
| 12.70 | 28.00 | 3.47 | 2.64 | 2.09 | 0.48 |

[1] The average of the absolute value of the difference between the measured reference volumes estimated from MRI.

[2] The average of the difference between the measured reference volumes and the volume estimated from MRI.

| Knee Sample # | Tool diameter (mm) | # defects | Average %Absolute error | | Average %Error | |
|---|---|---|---|---|---|---|
| | | | Depth | Wax | Depth | Wax |
| 1 | 6.35 | 6 | 8.45 | 9.41 | 1.68 | 0.25 |
| | 9.525 | 3 | 4.07 | 3.03 | 2.02 | 3.03 |
| | 12.7 | 3 | 1.52 | 1.93 | 0.83 | 0.94 |
| 2 | 6.35 | 4.00 | 7.06 | 9.58 | 1.34 | 5.21 |
| | 9.53 | 3.00 | 15.85 | 4.05 | 15.85 | 0.79 |
| | 12.70 | 3.00 | 3.95 | 2.49 | 3.95 | 2.49 |
| 3 | 6.35 | 6.00 | 9.44 | 4.62 | 2.76 | 1.31 |
| | 9.53 | 3.00 | 4.01 | 5.29 | 2.24 | 1.13 |
| | 12.70 | 3.00 | 0.89 | 0.76 | 0.85 | 0.76 |
| 4 | 6.35 | 6.00 | 9.62 | 6.76 | 4.43 | 4.90 |
| | 9.53 | 6.00 | 7.50 | 9.28 | 2.60 | 4.04 |
| | 12.70 | 2.00 | 7.37 | 1.42 | 7.37 | 1.42 |
| 5 | 6.35 | 4.00 | 6.96 | 7.74 | 2.02 | 3.23 |
| | 9.53 | 3.00 | 7.56 | 11.72 | 3.85 | 4.00 |
| | 12.70 | 3.00 | 6.38 | 1.14 | 4.66 | 0.21 |
| 6 | 6.35 | 7.00 | 10.88 | 4.78 | 8.85 | 2.12 |
| | 9.53 | 4.00 | 11.38 | 6.75 | 1.12 | 6.75 |
| | 12.70 | 3.00 | 3.54 | 1.46 | 3.54 | 0.13 |
| 7 | 6.35 | 8.00 | 5.33 | 6.62 | 0.89 | 1.84 |
| | 9.53 | 3.00 | 8.75 | 3.68 | 1.93 | 3.68 |
| | 12.70 | 3.00 | 8.18 | 4.59 | 7.77 | 1.97 |
| 8 | 6.35 | 7.00 | 14.91 | 10.24 | 1.24 | 0.95 |
| | 9.53 | 4.00 | 4.62 | 0.58 | 3.59 | 0.58 |
| | 12.70 | 3.00 | 3.94 | 10.36 | 1.12 | 0.40 |
| 9 | 6.35 | 10.00 | 16.47 | 6.69 | 3.55 | 1.16 |
| | 9.53 | 3.00 | 3.36 | 4.91 | 3.36 | 0.32 |
| | 12.70 | 3.00 | 1.60 | 1.65 | 1.16 | 1.02 |
| 10 | 6.35 | 7.00 | 10.54 | 0.08 | 6.76 | 0.08 |
| | 9.53 | 3.00 | 4.75 | 2.74 | 2.55 | 2.74 |
| | 12.70 | 2.00 | 3.78 | 1.09 | 3.78 | 1.09 |

*FIG. 13*

METHODS AND DEVICES FOR QUANTITATIVE ANALYSIS OF BONE AND CARTILAGE

CROSS-REFERENCE TO RELATED APPLICATIONS

This application claims the benefit of priority to U.S. patent application No. 61/152,440 entitled "Methods and Devices for Quantitative Analysis of Bone and Cartilage Defects" filed Feb. 13, 2009, which is incorporated by reference herein.

TECHNICAL FIELD

This application relates to analysis of bone for determining quantitative measurements of bone defects, and more particularly to systems and methods using wax casts to determine quantitative information regarding bone defects.

BACKGROUND ART

Osteoporosis and other bone disease and bone defects affect a relatively large segment of the population. In many such instances, the subject experiences pain, discomfort, loss of mobility, and increased risk of bone fracture or breakage. Osteoporosis and other bone disease and defects can occur in both human and animal subjects (e.g. horses). The National Osteoporosis Foundation estimates that as many as 44 million Americans are affected by osteoporosis and low bone mass. In 1997, the estimated cost for osteoporosis related fractures was $13 billion. That figure increased to $17 billion in 2002 and is projected to increase to $210-240 billion by 2040. Currently it is expected that one in two women over the age of 50 will suffer an osteoporosis-related fracture. Added to the number of non-osteoporosis related bone disease and defects, the severity of bone related disease and defects is clearly a major concern.

X-rays and other radiographic analysis are important diagnostic tools used to determine the extent and severity of bone disease and defects. However, in some instances, the need for verification of the image diagnostics and/or information in addition to the image diagnostics are required, for example, when conducting a clinical trial of a medical device or developing a medical device.

SUMMARY

One aspect of the claims below is a method for measuring a defect in a joint within a subject, comprising surgically accessing an articular surface of the joint with a defect; generating a physical model of the defect; and measuring a parameter of the defect from the cast.

Various embodiments of this aspect may include one or more of the following. The physical model can be made of wax. There can be multiple physical models for multiple defects of the joint, and each physical model can correspond to one defect of the multiple defects. The parameters measured can be one or more of height, width, depth, diameter, volume, area, surface area, or a surface feature. Also, multiple parameters can be measured and compared. The physical model can be altered or modified and a parameter can be measured from the altered or modified physical model. The physical model can be a cast, a mold or some other similar device. The parameter can be derived directly from the physical model, but can also be derived indirectly from the physical model, such as in the case of a parameter calculated in whole or in part from other measurements or parameters of the model, in part from other measurements or parameters taken other information, in part or in whole from a second virtual or physical model derived from the parameter or from some other indirect method.

Measuring the parameter can be done in various ways, for example, the physical model can be altered into another shape (e.g., rolled into a cylindrical shape), and placed in a pipette filled with a fluid such as alcohol. The volume of the model can then be measured by measuring the displacement of the fluid in the pipette.

Another aspect is a method for verifying indirect measurements of parameters associated with a defect of a joint using a physical model of the defect comprising the following. A physical model of the defect can be generated directly from the joint; a parameter of the defect can be derived from the physical model; and the parameter can be compared to a corresponding parameter of the defect that is derived from imaging data of the joint.

Various embodiments of this aspect may include one or more of the following. The physical model can be made of wax. There can be multiple physical models for multiple defects of the joint, and each physical model can correspond to one defect of the multiple defects. The parameters measured can be one or more of height, width, depth, diameter, volume, area, surface area, or a surface feature. Also, multiple parameters can be measured and compared. The physical model can be altered or modified and a parameter can be measured from the altered or modified physical model. The physical model can be a cast, a mold or some other similar device. The parameter can be derived directly from the physical model, but can also be derived indirectly from the physical model, such as in the case of a parameter calculated in whole or in part from other measurements or parameters of the model, in part from other measurements or parameters taken other information, in part or in whole from a second virtual or physical model derived from the parameter or from some other indirect method. Similarly, the corresponding parameter can be measured directly using data from a virtual model (such as, e.g., a digital computer model) or the corresponding parameter can be measured indirectly, for example, by calculation and/or by combinations of other parameters.

Another aspect is a method of measuring a parameter associated with a defect of a joint using a physical model of the defect, comprising the following. A physical model of the defect can be generated directly from the joint; the model can then be altered or modified; a parameter of the defect can be derived from the altered model; and the parameter can be compared to a corresponding parameter of the defect that is derived from imaging data of the joint.

Various embodiments of this aspect may include one or more of the following. The physical model can be made of wax. There can be multiple physical models for multiple defects of the joint, and each physical model can correspond to one defect of the multiple defects. Multiple parameters can be measured and compared. The physical model can be a cast, a mold or some other similar device. The parameter can be derived directly from the physical model, but can also be derived indirectly from the physical model, such as in the case of a parameter calculated in whole or in part from other measurements or parameters of the model, in part from other measurements or parameters taken other information, in part or in whole from a second virtual or physical model derived from the parameter or from some other indirect method. Similarly, the corresponding parameter can be measured directly using data from a virtual model (such as, e.g., a digital computer model) or the corresponding parameter can be measured indirectly, for example, by calculation and/or by combinations of other parameters.

Another aspect is a method for verifying a model of a defect in a joint comprising the following. A model of the defect is created; a corresponding parameter of the defect is derived from the model; and a model of the joint that includes the defect is created from image data of the joint; a corresponding parameter associated with the defect is derived from the model; and the parameter is compared to the corresponding parameter.

Various embodiments of this aspect may include one or more of the following. The model can be made of wax. There can be a single model for multiple defects of the joint. The parameters measured can be one or more of height, width, depth, diameter, volume, area, surface area, or a surface feature. Also, multiple parameters can be measured and compared. The model can be altered or modified and a parameter can be measured from the altered or modified model. The model can be a cast, a mold or some other similar device. The parameter can be derived directly from the model, but can also be derived indirectly from the model, such as in the case of a parameter calculated in whole or in part from other measurements or parameters of the model, in part from other measurements or parameters taken other information, in part or in whole from a second virtual or physical model derived from the parameter or from some other indirect method. Similarly, the corresponding parameter can be measured directly using data from a virtual model (such as, e.g., a digital computer model) or the corresponding parameter can be measured indirectly, for example, by calculation and/or by combinations of other parameters.

BRIEF DESCRIPTION OF THE DRAWINGS

The embodiments discussed in the present application will be more readily understood by reference to the following detailed description, taken with reference to the accompanying drawings, in which:

FIG. 13 is a table summarizing the results shown in FIG. 12 for each knee sample in that analysis, in accordance with an embodiment of the invention.

DETAILED DESCRIPTION OF SPECIFIC EMBODIMENTS

In illustrative embodiments, systems and methods for quantifying cartilage and joint defects are presented. The method may include, for example, generating a wax mold or cast of the defect within the cartilage or joint. The systems and methods described herein may then be used to determine certain parameters and features of the wax mold/cast in order to quantify the cartilage and/or joint defects. Details of illustrative embodiments are discussed below.

Figure 2:
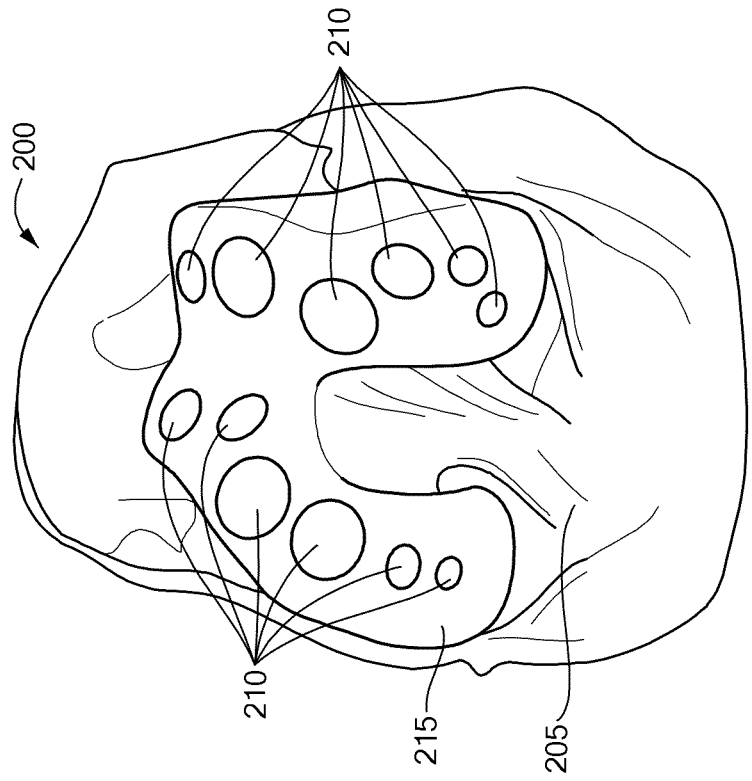
FIG. 2 is a perspective diagram showing the distal end of an exposed femur of an exemplary knee having cartilage and bone defects to be measured about the femoral condyles of the femur.
Figure 1:
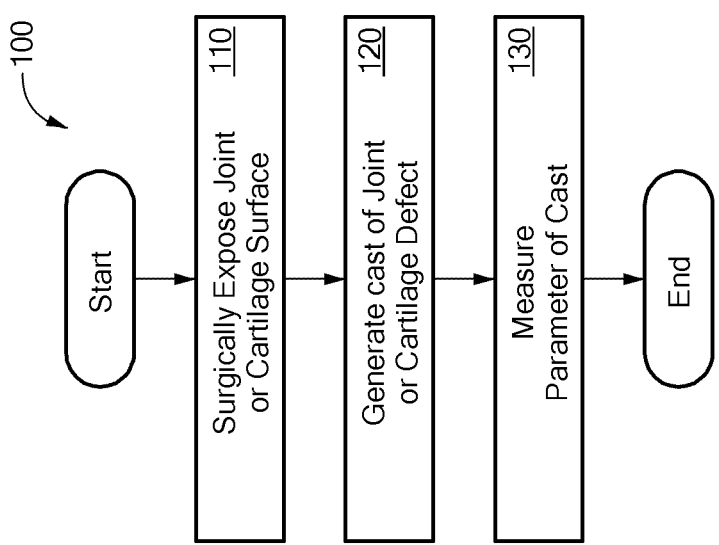
FIG. 1 is flowchart showing the steps for measuring defects in cartilage, in accordance with an embodiment of the invention.

FIG. 1 is a flowchart illustrating a method of measuring defects in a bone, cartilage, or a joint, in accordance with some embodiments. In particular, the method 100 generally involves a three step process. First, a medical practitioner (e.g., a surgeon) may surgically expose the bone, cartilage, or joint of interest (Step 110). An exemplary exposed joint 200 is shown in FIG. 2. As seen in FIG. 2, the knee joint includes the condyles 215 at the distal end of a femur, which is surrounded by various skin, ligament, and other tissues 205. The condyles 215 have a variety of defects 210. In this example, the joint of interest is the knee joint 200 and the defects were man-made using a drill. However, natural defects within any joint, bone, or cartilage can also be measured.

Figure 4:
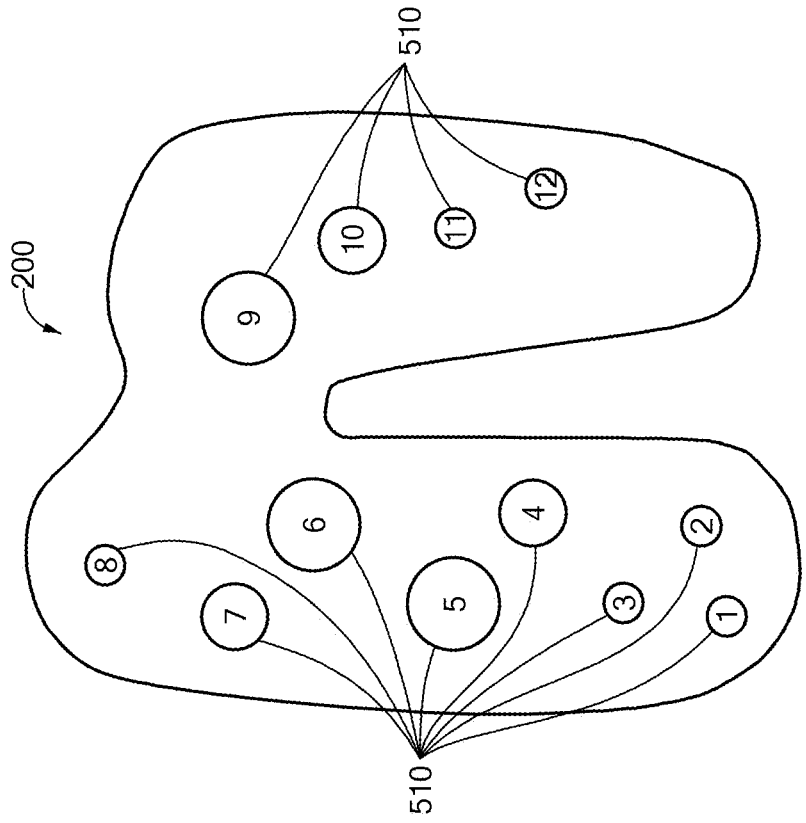
FIG. 4 is a schematic diagram of an axial view of a distal end of the femur in FIG. 2 having wax casts within each of the bone and cartilage defects, in accordance with an embodiment of the invention.

Once the joint is exposed, casts or molds of the cartilage, bone and joint defects (step 120) can be generated and various parameters of the cast can be measured in order to obtain information regarding the defect (Step 130). For example, the medical practitioner may measure the height, width, depth, diameter, volume, area, surface area, and/or surface features, to name but a few parameters. FIG. 4 shows a knee joint with casts 510 in the defects 210. It is important to note that, because the casts are nearly identical inverse molds of the defects, the cast parameters measured will provide quantitative information on the defect itself. A variety of cast parameters may be measured, including, for example, the volume of the cast and, thus, the volume of bone defects 210.

Figure 3:
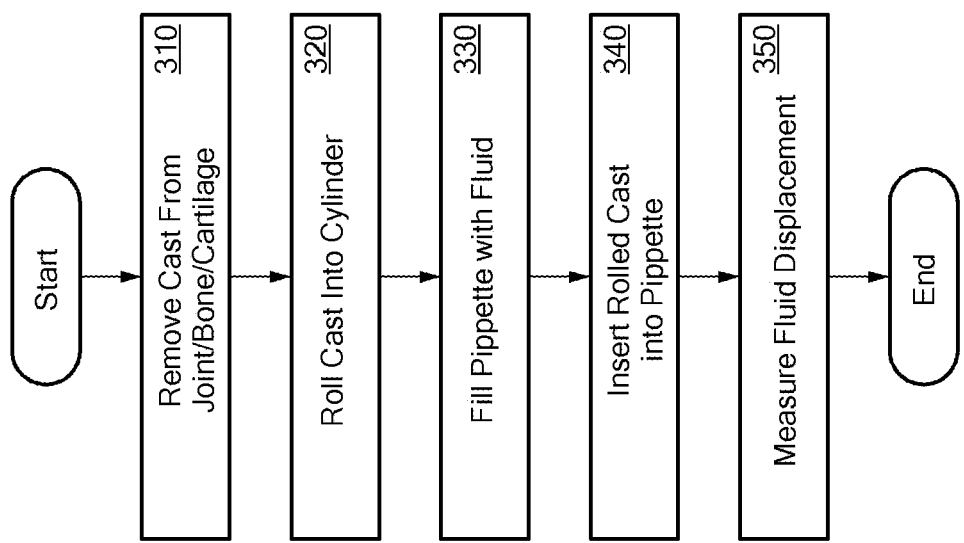
FIG. 3. is a flowchart showing steps of measuring the cartilage and bone defects shown in FIG. 2 using wax casts, in accordance with an embodiment of the invention.

FIG. 3 is a flowchart that illustrates such a method. In particular, once the cast 510 is generated (step 120 in FIG. 1), it may be removed from the joint (step 310). Once removed from the joint, the medical practitioner or technician can roll the cast into a cylinder (step 320).

Figure 5A:
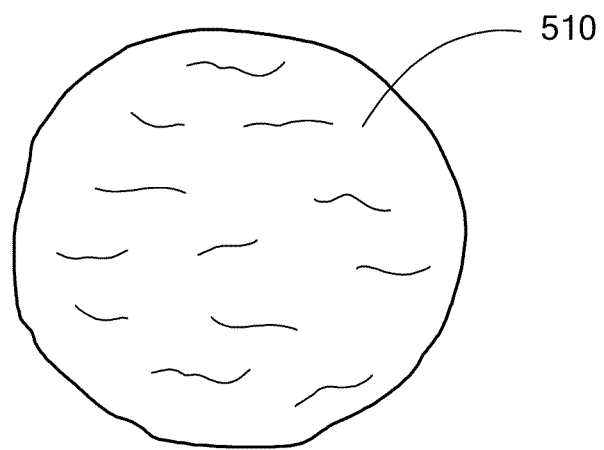
FIG. 5a is a perspective view of a wax cast, in accordance with an embodiment of the invention.
Figure 5B:
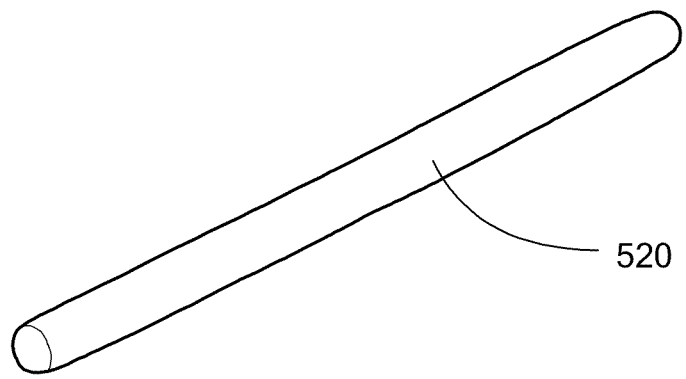
FIG. 5b is a perspective view of the wax cast of FIG. 5a after the cast has been rolled.

FIGS. 5a and 5b show an example of a cast 510 removed from the joint 510 and an example of the cast 520, after it has been rolled to measure its volume. It is important to note that, if additional parameters are required (e.g., length, width, diameter, etc.), the medical practitioner or technician should measure them prior to rolling the cast 520. Alternatively, the volume of the cast can be measured without rolling the cast, by using appropriately-sized measuring devices. However, rolling the cast is preferred, as it will allow the cast to be inserted in a pipette having a smaller diameter and providing more precise measurements than may be achieved, for example, with a pipette of a large diameter.

After the cast is rolled, the medical practitioner or technician may then fill a pipette 530 with a liquid to a fixed baseline volume level (step 330). A variety of fluids can be used to fill the pipette 530. For example, the medical practitioner or technician can use water, saline, or alcohol, to name but a few. Additionally, a variety of different size pipettes can be used, and may vary depending on the size of the defect involved. For example, for the knee example described herein, the pipette 530 can be a 1 milliliter pipette having $1/100$ milliliter graduations.

To measure the volume of the cast 510 and, thus, the defect 210, the rolled wax cast 510/520 can be inserted into the filled pipette (step 340) and the fluid displacement measured with respect to the baseline level (step 350). The fluid displacement with respect to the baseline level represents the volume of the cast 520 and, thus, the bone/cartilage defect 210. For example, if the medical practitioner/technician fills the pipette 530 to a baseline volume of 0.250 ml and the total volume within the pipette 530 after insertion of the rolled cast 520 is 0.300 ml, the fluid displacement (and thus the volume of the cast and defect) is 0.050 ml. In other words, the volume of the defect 210 is 0.050 ml or 50 cubic millimeters.

Although a variety of materials can be used to generate defect molds/casts, some embodiments utilize materials that create soft molds/casts so that the molds/casts may be rolled into a cylinder once removed from the bone/cartilage. Therefore, for example, wax is preferably used instead of ceramics or plastics that harden as they cure or cool, but other materials, including such ceramics or plastics could also be used in alternate embodiments. Additionally, to prevent damage to the bone, cartilage, or joint, materials with melting temperatures that are lower than temperatures that may burn tissue are preferred.

Other parameters of the cast 510 can be measured in more traditional ways. For example, the thickness, depth, height, width, diameter, etc. can be measured using calipers. These measurements can then be used in conjunction with various mathematical formulas to calculate the surface area, cross-sectional area, etc.

Figure 6:
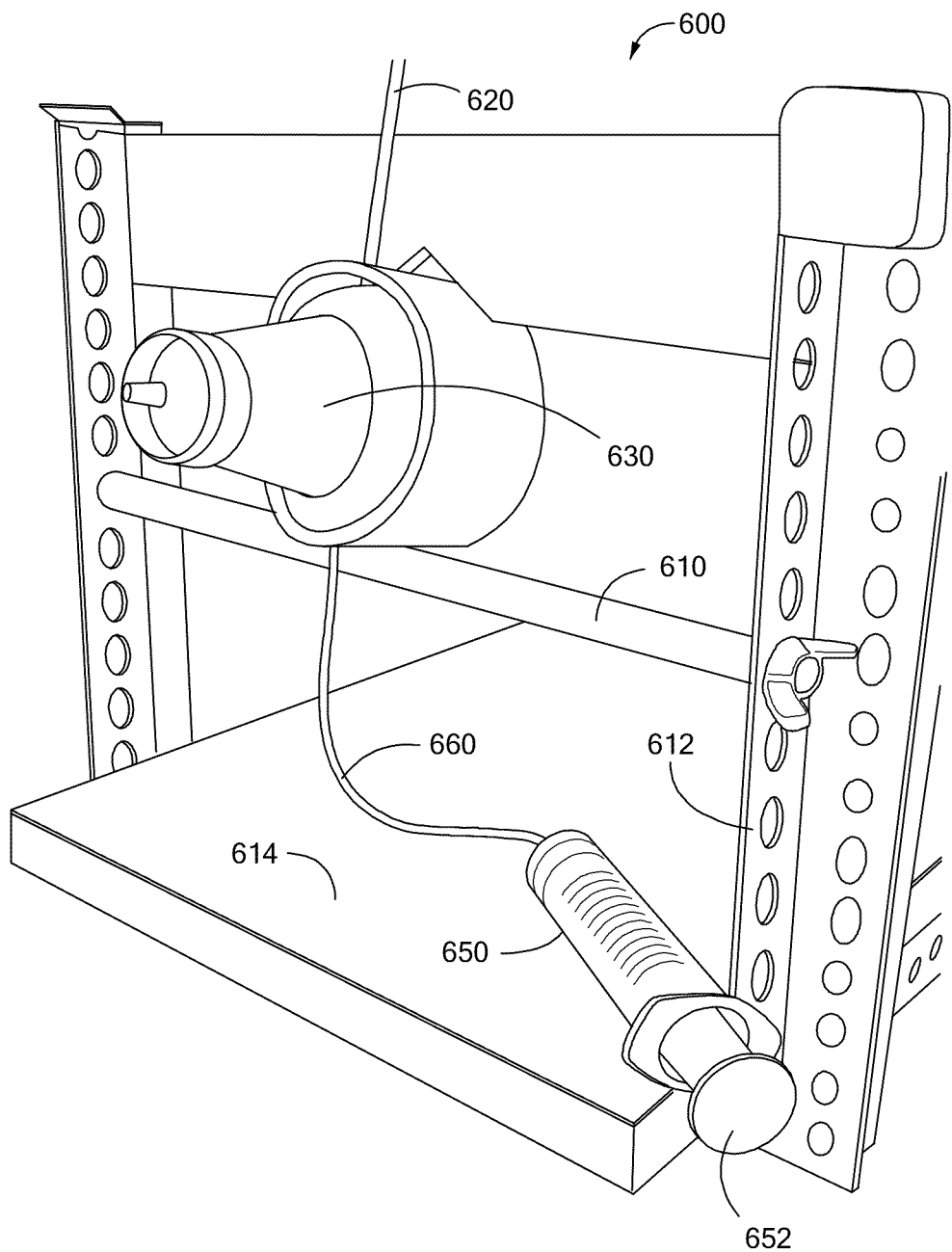
FIG. 6 is a side perspective view of an exemplary system for measuring parameters of the wax casts, such as those shown in FIGS. 5a and 5b, in accordance with an embodiment of the invention.
Figure 7:
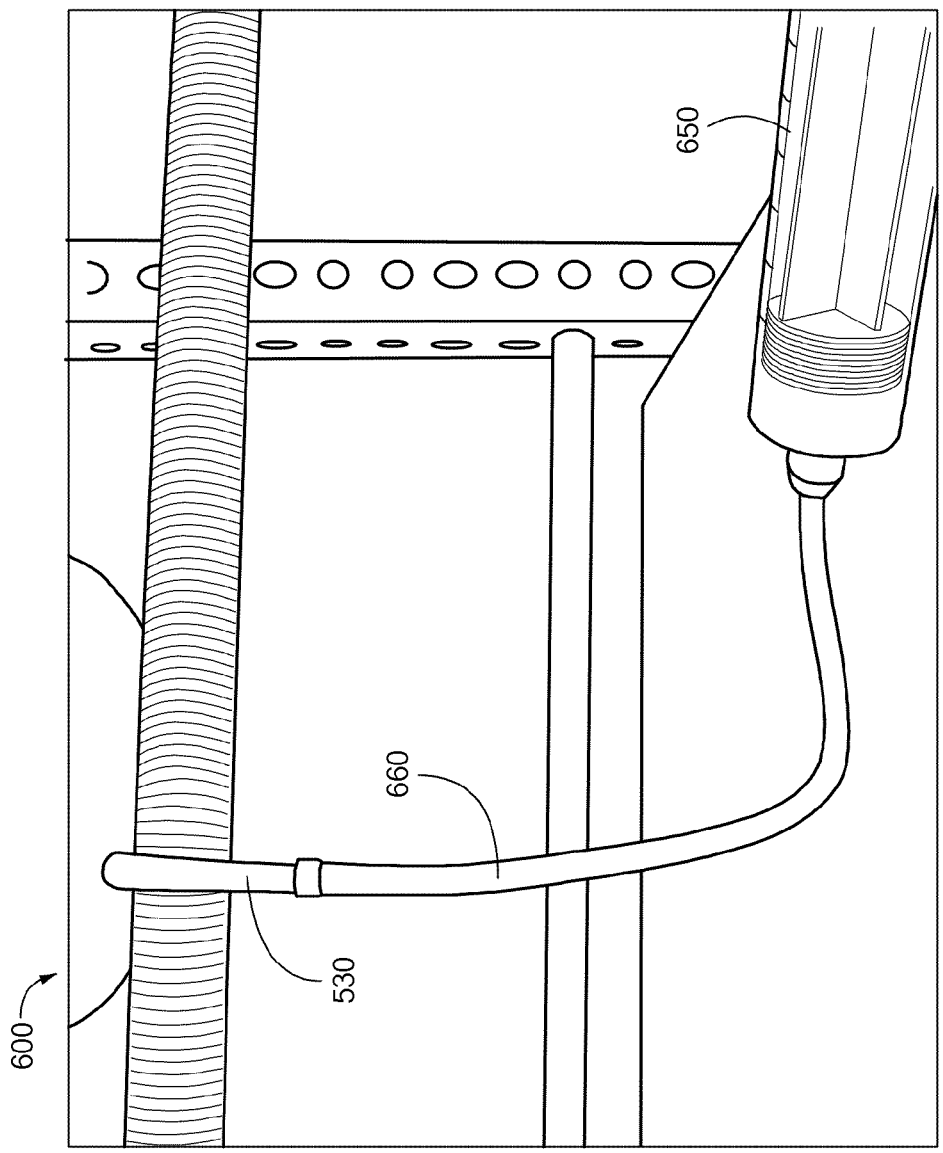
FIG. 7 is a side perspective view of a portion of the system of FIG. 6 that is used to fill a pipette of the system, in accordance with an embodiment of the invention.
Figure 8:
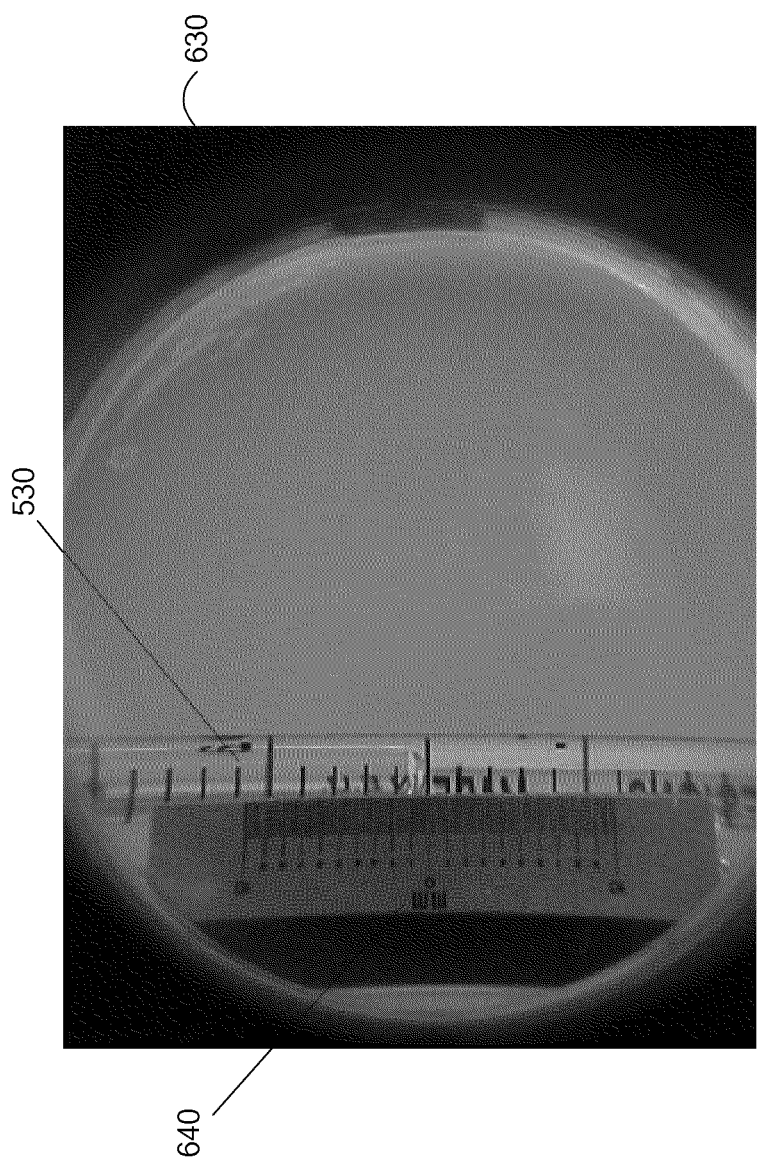
FIG. 8 is a photograph of the view of the pipette through the magnifying device of a system similar to that shown in FIG. 6, in accordance with an embodiment of the invention.

FIGS. 6-8 schematically show an apparatus/system 600 that may be used to help perform the method described above. The apparatus can include a support structure 610 that supports the various components required to measure the parameters of the cast 510. For example, the support structure 610 may be a stand 612 or other appropriate structure with a base 614. The support structure 610 may also have a pipette holder 620 that receives and holds the pipette 530 upright. As is known in the art, to achieve accurate pipette measurements, the pipette should be upright. To aide the user in viewing and accurately measuring the level within the pipette (e.g., the baseline level and the level after inserting the rolled up cast), the apparatus 600 can also include a magnification device 630 such as a magnified viewfinder or a magnifying glass. Additionally or alternatively, as shown in FIG. 7, the apparatus 600 can also have an additional measurement device 640 that is separate from the graduations on the pipette 530. For example, the measuring device 640 may be a ruler or other device having 1 mm ($1/100$ ml) markings.

As mentioned above, before the rolled cast 520 is inserted into the pipette 530, the medical practitioner or technician may fill the pipette 530 to a baseline level. To that end, the apparatus 600 may also include a syringe 650. The syringe 650 may be filled with the fluid to be used to set the baseline level within the pipette (e.g., alcohol), and may be connected to one end of the pipette 530 using tubing 660. Therefore, when filling the pipette 530 to the baseline level, the user need only depress the syringe's plunger 652. The user may then adjust the amount of fluid within the pipette 530 by either depressing the plunger 652 further (e.g., to add additional fluid to the pipette 530 and increase the level) or pulling back the plunger 652 (e.g., to withdraw fluid and lower the level within the pipette 530). This allows a user to essentially "fine-tune" the amount of fluid within the pipette 530 and, thus, the baseline level.

It is important to note that some embodiments can be used to directly quantify parameters of cartilage, bone, and joint defects. Additionally or alternatively, the above described systems and method may be used verify and/or determine the accuracy of other analysis systems and methods. For example, some embodiments may be used to quantitatively measure the accuracy of cartilage defect measurements from MR images.

Figure 9:
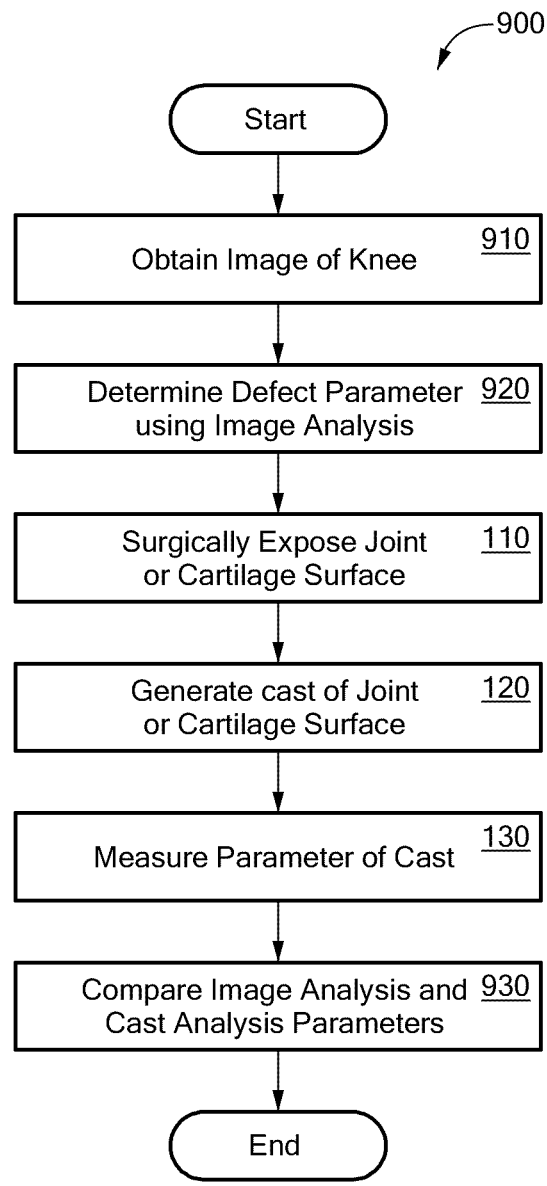
FIG. 9 is a flowchart showing an embodiments of a method to verify the accuracy of image based analysis of defects, in accordance with an embodiment of the invention.

FIG. 9 is a flowchart illustrating a method 900 of using the above described methods and systems to verify the accuracy of image based analysis. In particular, the method 900 first obtains an image of the bone, cartilage, or joint in question (Step 910). As is to be expected, the image should include the defects to be measured. Depending on the image analysis system, the image can be any one of a number of images. For example, the image may be an x-ray or MRI. Once obtained, the method 900 can then perform an image based analysis to determine the parameters of the defects contained within the image data (Step 920).

The accuracy of the imaging analysis and the parameters obtained in Step 920 can then be verified. In particular, the medical practitioner may surgically expose the bone/joint/cartilage of interest (Step 110), generate a wax cast of the defects on the bone/joint/cartilage (Step 120), and measure a parameter of the wax cast (Step 130). For example, the medical practitioner or a technician can roll the wax cast into a tube and measure the volume, as described above with respect to FIG. 3.

Once the parameters of the defects are determined using both the image analysis and the wax cast method, the method 900 may then compare the results of each analysis method (Step 930). As mentioned above, the wax casts 510 are essentially near identical reverse molds of the defects 210 within the bone/joint/cartilage, and, as seen in FIG. 5a, match the contours of the surface of the defect. Therefore, the measurements obtained by this method are highly accurate. Accordingly, by comparing the results from the image analysis method to the wax cast method, the accuracy of an image analysis method or system can be verified. In other words, if the image analysis system/method provides results that are identical or similar to those of the wax cast method/system, then the image analysis is likely accurate. However, if the image analysis method/system provides results that differ greatly from the wax cast method/system, then the image analysis method is likely not accurate.

EXAMPLE

Comparison of Image Processing and Analysis Tools

The below described study measures quantitatively the accuracy of targeted cartilage defect measurements from MR images using image processing and analysis tools. For this, a controlled before and after cartilage defect test scenario was implemented with ten cadaver knees.

For each cadaver knee, a baseline or pre-defect knee-MRI scan was acquired. The knee joint was then exposed and several defects of three different radii were bored within the femoral cartilage layer. Several measurements and wax casts were obtained from the defects in order to obtain reference volume measurements to which the MRI-based volume estimates could be compared.

After all measurements and wax casts were made, the knee joint was closed and a second MRI scan was acquired. Based on cartilage boundary segmentations from the MRI scan images, each defect was detected and its volume was estimated. The MRI based cartilage defect volume estimates were then compared to the corresponding reference volume measurements. A total of 128 cartilage defects were generated and analyzed.

Accuracy was evaluated by comparing the focal cartilage defect volumes through linear regression. As quantitative measures of accuracy, the minimum measurable volumes at 95% confidence level were estimated as well as average percent errors.

Based on results from all knee samples and defects generated, the estimated minimum volume interval measurable at 95% confidence level was approximately $\pm 16$ mm$^3$. Maximum values for average percent absolute error levels were approximately 10.5%, 7.3%, and 3.5% corresponding to defects of 3.175 mm, 4.76 mm and 6.35 mm respectively (average defect volumes of 50 mm$^3$, 125 mm$^3$ and 210 mm$^3$) thus showing in average error levels well within the minimum measurement accuracy interval of $\pm 16$ mm$^3$.

For each test case, two separate MRI scans were taken. The first MRI scan provided baseline images of the knee joint and cartilage tissue before any defects were generated. After the first MRI scan, the knee joint was opened and several circularly shaped cartilage defects of three different radii (3.175 mm, 4.76 mm and 6.35 mm) were generated on the medial and lateral femoral cartilage surfaces using a boring tool of known radius.

Each defect was generated within the cartilage layer and the depth of each defect was measured six times around the perimeter using a caliper accurate to 0.01 mm (Absolute Digimate, Mitutoyo Corp.). In addition to the depth measurements, wax casts were made of each one of the defects (FIG. 4). After all wax casts were removed and labeled for later measurement, the knee joint was rinsed several times with saline solution to reduce the presence of microscopic metallic traces and closed by suture. Saline solution was injected into the joint to eliminate possible air bubbles. The knee sample was then placed and sealed in double vacuum bags. A second, post-defect MRI scan was then acquired.

Two methods were applied to estimate the reference cartilage defect volumes defining the standard to which the MRI based defect volume estimates were compared. The first method estimated each reference defect volume based on the corresponding depth measurements and the known radius of the boring tool used to generate the defect. Specifically, each volume was calculated by integration of a cylindrical defect shape of known radius and height given by a linear or exponential least-squares fit of the depth measurements performed around the periphery of each cartilage defect. The fit (e.g. linear or exponential) with the largest F statistic (reflecting the confidence of the fit) was selected for each reference volume calculation.

The second method for reference volume data measurement was based on volume displacement of the wax casts made for each one of the defects. For this, each wax cast was rolled into a cylinder so that it could slide into a 1 ml ($\frac{1}{100}$ ml markings) measuring pipette. The pipette was placed in a holder with additional measurement markings ($\frac{1}{100}$ ml markings) and a magnified viewfinder. The pipette was then filled up to a fixed baseline volume level using a syringe filled with alcohol attached to the pipette from the bottom. The volume of each wax cylinder was then measured by sliding it into the pipette from the top and measuring the volume displacement with respect to the baseline level.

As standard procedure and for compatibility of results with any future clinical trial and implementation using human subjects, all MR imaging was performed on a whole body magnet operating at a field strength of 1.5 T (GE Signa) and following FDA radiofrequency absorption guidelines. Pulse sequences routinely used for knee MRI scans were used. Specifically, a rapid scout scan was acquired in the axial, coronal and sagittal planes using a gradient echo sequence to make sure of the proper positioning of the knee, followed by three-dimensional spoiled gradient-echo (3D SPGR) sequences in the sagittal and coronal planes. A total of 64 3D SPGR images were acquired for each view (i.e. sagittal, coronal) and scan. The images were 512 by 512 pixels in size at 0.27 mm by 0.27 mm pixel resolution and 1.5 mm slice image spacing providing complete coverage across the knee joint in both mediolateral and antero-posterior views while achieving good spatial resolution and contrast-to-noise ratios between cartilage, bone and joint fluid.

Image processing software and procedures were used to analyze the MR images of the knee joint before and after cartilage defect. The volume of each defect was estimated from MR images based on segmentations of the cartilage regions from each slice in the corresponding MR scan and the estimation of the missing cartilage envelope.

The evaluation of the accuracy of the estimation process for cartilage defect volume was performed by comparing the estimated MRI-based cartilage defect volumes to the corresponding reference cartilage defect volumes using linear regression and percent error. MRI-based measurement accuracy was evaluated with respect to each of the two reference volume measurements acquired (depth and wax volume displacement measurements). The two types of reference volume measurements were also compared to each other in order to obtain an estimate of the associated error.

As an quantitative measure of absolute accuracy for MRI based volume estimates, the minimum measurable volume was obtained based on the volume estimation interval at 95% confidence. Average percent error levels for signed and absolute error values were calculated for evaluation of variability and average accuracy in terms of bias (for signed errors) and average spread (for absolute errors)

The following summary of the results for the measurement and estimation of cartilage defect volumes is focused on showing the accuracy of MRI based extraction and estimation of cartilage defect volumes.

Figure 10:
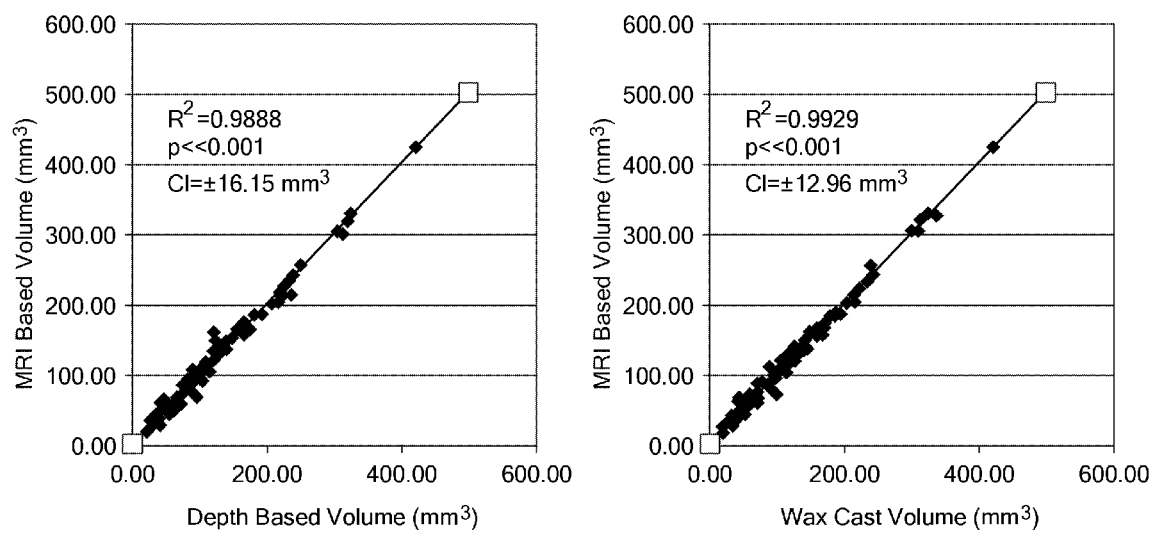
FIG. 10 is a graph showing the estimated volume distribution and the corresponding linear fit for all cartilage defects analyzed in an exemplary analysis with respect to the depth-based and wax volume displacement reference volume measurements, in accordance with an embodiment of the invention.

FIG. 10 shows the estimated volume distribution and the corresponding linear fit for all cartilage defects analyzed with respect to the depth-based and wax volume displacement reference volume measurements. The associated R$^2$, p-value and confidence intervals are shown. The reference volumes obtained by the two measurement methods used are compared in FIG. 11.

Figures 11, 12:
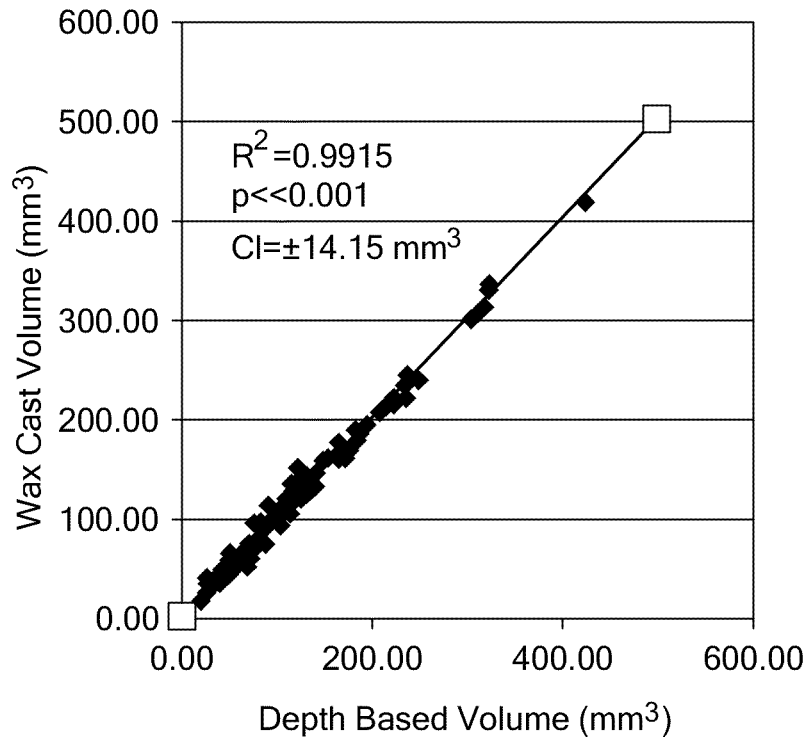
FIG. 11 is a graph showing the comparison of the reference volumes obtained by two measurement methods, in accordance with various embodiments of the invention.
FIG. 12 is a table summarizing the results of an exemplary analysis as a function of boring tool diameter, in accordance with an embodiment of the invention.

FIG. 12 summarizes the results as a function of the boring tool diameters used to generate the cartilage defects for all knees. FIG. 13 summarizes the corresponding results for each sample knee.

An analysis was conducted to estimate the accuracy of targeted cartilage defect volume measurement from MRI scans of the knee. For this, a controlled experimental setup for the generation and measurement of targeted cartilage defects was implemented using 10 cadaver knee samples. Several cylindrical defects of three different radii (3.175 mm, 4.76 mm and 6.35 mm) and variable depth were generated on each knee. Each cartilage defect volume was estimated based on MRI scans and compared to corresponding reference measurements performed using two different physical methods (defect depth and volume displacement of defect wax casts).

Accuracy was evaluated by comparing the focal cartilage defect volumes through linear regression. As a quantitative measure of absolute accuracy for MRI based volume estimates, the minimum measurable volume was obtained based on the volume estimation interval at 95% confidence.

The estimation and accuracy levels of defect volumes from MRI may be limited by the accuracy levels of the corresponding reference volume measurements to which they are compared. Based on the plot in FIG. 11, the reference volumes can be estimated to an accuracy of approximately ±14 mm$^3$ at a 95% confidence level, thus setting a lower threshold on the accuracy level estimation of MRI-based volumes. Comparing MRI-based measurements to each of the two different reference volume type measurements resulted in accuracy levels of ±16 mm$^3$ (with respect to depth based measurements) and ±13 mm$^3$ (with respect to wax-volume displacement measurements). While the accuracy levels obtained with respect to each reference volume measurement method were comparable, a paired t-test analysis showed that the corresponding error distributions were different with a t-score of 3.2 and p=0.002. Thus, although the accuracy levels attained with respect to each reference volume type were comparable, the slightly lower accuracy level obtained with respect to depth measurements can be due to higher variability in the estimation of the reference volumes based on a limited number of depth measurements.

Average percent error levels for signed and absolute error values were calculated for evaluation of variability and average accuracy in terms of bias (for signed errors) and average spread (for absolute errors). The results summarized in FIG. 12 show that maximum values for average percent absolute error levels were approximately 10.5%, 7.3%, and 3.5% corresponding to defects of 3.175 mm, 4.76 mm and 6.35 mm respectively. While the results shown in FIG. 13 summarizing the measurements for each of the ten knee samples, show that in some cases there were absolute errors as high as 16%, an examination of the specific cases showed that most of the largest errors were found to be associated with cartilage defects showing metallic artifacts in the MRI scans (caused by the boring tools used to generate the defects) thus biasing the estimation and segmentation of the defect boundaries or there was a larger discrepancy between reference measurement values thus pointing to less reliable reference measurements. In general, considering the average defect volumes of 50 mm$^3$, 125 mm$^3$ and 210 mm$^3$ corresponding to each of the three defect diameters generated, the average error levels obtained based on the average percent error levels shown in table 1, are well within the minimum measurement accuracy interval of ±16 mm$^3$.

The results showed a good cartilage defect measurement accuracy performance when compared to the magnitude of the cartilage volumes generated and supporting the feasibility of using MRI to estimate cartilage defect volumes.

The embodiments described above are intended to be merely exemplary, and numerous variations and modifications of the invention will be apparent to those skilled in the art. All such variations and modifications are intended to be within the scope of the claims.

What is claimed is:

1. A method for evaluating accuracy of an image analysis process for indirect measurements of parameters associated with a cartilage defect of a joint using image data of the joint, comprising:
    generating a physical model of the cartilage defect from the joint, wherein the physical model includes a wax model;
    deriving a volume of the cartilage defect from the wax model using fluid displacement;
    comparing the volume to a corresponding parameter of the cartilage defect, wherein the corresponding parameter is derived from the image data of the joint, and
    determining the accuracy of the image analysis process for deriving the corresponding parameter.

2. The method of claim 1, further comprising measuring a second parameter from the wax model.

3. The method of claim 2, wherein the second parameter is derived directly from the wax model.

4. The method of claim 2, wherein the second parameter is derived indirectly from the wax model.

5. The method of claim 1, further comprising altering the wax model prior to measuring the volume.

6. The method of claim 1, further comprising:
    altering the wax model; and
    measuring a second parameter from the altered wax model.

7. The method of claim 1, wherein deriving the volume further comprises:
    rolling the wax model into a cylinder;
    filling a pipette with a fluid such that the pipette is filled to a fixed baseline volume;
    inserting the rolled cylinder into the filled pipette such that the fluid within the pipette is displaced; and
    measuring the fluid's volume displacement within the pipette with respect to the baseline volume.

8. The method of claim 7, wherein the fluid is alcohol.

9. The method of claim 1, further comprising generating multiple physical models for multiple defects of the joint.

10. The method of claim 9, wherein each physical model corresponds to one defect of the multiple defects.

11. The method of claim 1, further comprising measuring a second parameter from the physical model.

12. The method of claim 11, wherein the second parameter is a measure of a height, a width, a depth, a diameter, a volume, an area, a surface area, a surface feature, or combinations thereof.

13. The method of claim 11, wherein the second parameter is derived directly from the physical model.

14. The method of claim 11, wherein the second parameter is derived indirectly from the physical model.

15. The method of claim 1, further comprising altering the physical model prior to measuring the volume.

16. The method of claim 1, further comprising:
    altering the physical model; and
    measuring a second parameter from the altered physical model.

17. The method of claim 1, wherein the physical model includes a cast or a mold.

18. The method of claim 1, wherein the corresponding parameter is derived directly from a digital model derived from the image data of the joint.

19. The method of claim 1, wherein the corresponding parameter is derived indirectly from a digital model derived from the image data of the joint.

* * * * *